United States Patent [19]

Anderson et al.

[11] Patent Number: 5,126,326
[45] Date of Patent: Jun. 30, 1992

[54] ENZYME INHIBITING PEPTIDE DERIVATIVES

[75] Inventors: Paul C. Anderson, Pierrefonds; Yvan Guindon, Montreal; Christiane Yoakim, Laval, all of Canada

[73] Assignee: Bio-Mega, Inc., Laval, Canada

[21] Appl. No.: 361,895

[22] Filed: Jun. 6, 1989

[51] Int. Cl.$^5$ .................. C07K 5/06; A61K 37/02
[52] U.S. Cl. ........................ 514/17; 514/18; 530/329; 530/330; 530/331
[58] Field of Search ............. 530/329, 330, 331; 514/17, 18

[56] References Cited

FOREIGN PATENT DOCUMENTS 76241 7/1987 Australia.
77028 4/1983 European Pat. Off..
2986 5/1987 PCT Int'l Appl..
2203740 10/1988 United Kingdom.

OTHER PUBLICATIONS

Moore et al., Bioch. & Biophys. Res. Comm. 159(2), pp. 420-425 (1989).
Richards et al., FEBS Letters 247(1), pp. 113-116 (1989).
Seelmeier et al., PNAS vol. 854, pp. 6612-6616 (1988).

Primary Examiner—Robert W. Ramsuer
Assistant Examiner—M. S. H. Gabilan
Attorney, Agent, or Firm—David E. Frankhouser; Daniel Reitenbach; Mary-Ellen Timbers

[57] ABSTRACT

Disclosed herein are peptide derivatives which inhibit the activities of human immunodeficiency virus (HIV) protease and renin. The peptide derivatives can be represented by general formula $R^1-R^2-Y-R^3-R^4$ wherein $R^1$ is a derived amino acid based on an $O^4$-(carboxymethyl)-tyrosyl residue, $R^2$ and are amino acid or analogous amino acid residues ($R^3$ may optionally be absent), Y is a non-peptide linking unit, e.g. statyl, and $R^4$ is $[-NR^{17}CHR^{18}-C(O)]_p-Z$ wherein $R^{17}$ is hydrogen or lower alkyl, $R^{18}$ is an amino acid or analogous amino acid side chain, p is zero or one and Z is a terminal group (e.g. hydroxy or amino), or $R^4$ is $-NR^{17}CR^{18}(R^{21})CH_2OH$ wherein $R^{17}$ and $R^{18}$ are as noted hereinabove and $R^{21}$ is hydrogen, lower alkyl or hydroxy(lower)alkyl. The derivatives are useful as agents for combatting HIV infections and for treating renin-associated hypertension and congestive heart failure.

2 Claims, No Drawings

ENZYME INHIBITING PEPTIDE DERIVATIVES

FIELD OF THE INVENTION

This invention relates to compounds having valuable pharmacological properties. More specifically, the invention relates to peptide derivatives (hereinafter called "peptides") exhibiting activity against particular retroviruses, to processes for producing the peptides, to pharmaceutical preparations thereof, and to a method of using the peptides to combat infections caused by the retroviruses. The invention also includes pharmaceutical formulations and a method of treatment for renin-associated hypertension and for congestive heart failure wherein the peptides serve as the active agent.

BACKGROUND OF THE INVENTION

During the last ten years, retroviruses have emerged from relative obscurity to prominence. These viruses now are known to cause of variety of diseases in vertebrates, the most insidious to humans being immunodeficiencies and cancers.

In 1983, a retrovirus, known as human immunodeficiency virus type 1 (HIV-1), was established as a causative agent for acquired immune deficiency syndrome (AIDS). This virus has become a pestilence of alarming proportion. More recently, the closely related virus, human immunodeficiency virus type 2 (HIV-2) has been identified as a second causitive agent of AIDS. (Hereinafter, the term "HIV" is meant to include both HIV-1 and HIV-2 and any mutants thereof).

Presently, several compounds are being evaluated in the clinic as possible therapeutic agents for AIDS. Another compound, 3'-azido-3'-deoxythimidine (known also as zidovudine or AZT), has been shown in the clinic to decrease mortality and the frequency of opportunistic infections in AIDS patients. This latter compound is being used to manage certain patients with symptomatic HIV infections. However, in spite of some recent progress, the need for an effective therapy for AIDS still exists. For recent reviews, see R. A. Weiss in "Molecular Basis of Virus Disease", Symposium of the Society for General Microbiology, Vol. 40, Eds. W. C. Russel and J. W. Almond, University Press, Cambridge, UK, 1987, pp 167-192, and R. C. Gallo and L. Montagnier, Scientific American, 259, (4), 40 (1988).

One approach to finding agents having anti-HIV activity is to inhibit the action of HIV-encoded enzymes. This manner of inhibition interferes with the replication and propagation of the virus. Such an approach has been applied successfully in a search for inhibitors of the viral encoded enzyme, reverse transcriptase (RT). More explicitly, the previously noted zidovudine was found to inhibit RT which is required to effect viral replication. Subsequently, zidovudine was developed as an anti-HIV agent. Still more recently, this approach has been investigated using another HIV-encoded enzyme known as HIV protease as the target enzyme. In one instance, pepstain A was found to inhibit the intracellar processing that provides the requisite HIV protease. See, S. Seelmeier et al., Proc. Natl. Acad. Sci. USA, 85, 6612 (1988). However, the development of pepstatin A as an anti-HIV agent seems improbable in view of its multiple activities. In another instance, M. L. Moore et al., Biochem. Biophys. Res. Comm., 159, 420 (1989), reported on investigations showing the inhibition of HIV protease by three heptapeptide analogs modeled after a conserved cleavage site (gag gene region) of the viral genomic polyprotein. A. D. Richards et al., FEBS Letters, 247, 113(1989), also have reported in vitro inhibition of HIV protease be acetylpepstatin and a nonapeptide analog.

The present application discloses a group of peptide derivatives which are potent inhibitors of HIV protease and renin. These attributes, together with the attributes of a relatively selective action and an apparent lack of toxicity, renders the peptides useful as agents for combating HIV infections and for treating renin-associated hypertension and congestive heart failure.

The present peptides of this application are distinguished readily from pepstatin A and the previously noted peptide analogs by chemical and biochemical differences. The present peptides also possess a partial structural resemblance to peptide derivatives reported to be renin inhibitors; for instance, see D. F. Veber et al., European patent application 77,028, published Apr. 20, 1983, and A. Wagner et al., Australian patent application 76241/87, published Feb. 4, 1988. The remaining structural features and differences in biological profiles distinguish these latter prior art compounds from the present peptide derivatives, notwithstanding the existence of broad generic disclosures, such as R. Ten Brink, PCT patent application WO87/02986, published May 21, 1987, encompassing a myriad of compounds ranging in the millions. Finally, a class of peptide isosteres have been reported recently to have the unusual combination of renin inhibitory and antiretroviral activities; the latter compounds have structures which are quite different from the present peptides (see B. Weidmann, UK patent application 2203740, published Oct. 26, 1988).

SUMMARY OF THE INVENTION

The peptides of this invention are represented by formula 1

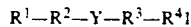

wherein $R^1$ is a derived amino acid radical of formula 2

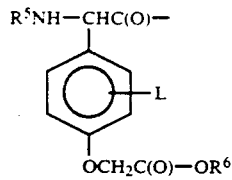

wherein $R^5$ is hydrogen, lower alkyl, or $R^7OC(O)$— or $R^7C(O)$— wherein $R^7$ is lower alkyl, lower cycloalkyl, (lower cycloalkyl)methyl, phenyl, phenyl monosubstitued with lower alkyl, lower alkoxy or halo, benzyl or benzyl monosubstituted with lower alkyl, lower alkoxy or halo; $R^6$ is hydrogen, lower alkyl, lower cycloalkyl, (lower cycloalkyl)methyl, phenyl, phenyl monosubstituted with lower alkyl, lower alkoxy or halo, benzyl, or benzyl monosubstituted with lower alkyl, lower alkoxy or halo; L on the aromatic ring of the radical of formula 2 represents hydrogen or a substituent on the aromatic ring, the substituent being selected from the group of lower alkyl, lower alkoxy and halo, or L represents the same or different of two substituents on the aromatic ring, the substituents being selected from the group of lower alkyl, lower alkoxy and halo, provided that any two substituents do not interfere with each others presence;

$R^2$ is —N($R^8$)CH($R^9$)C(O)— wherein $R^8$ is hydrogen or lower alkyl and $R^9$ is hydrogen, lower alkyl, lower alkyl monosubstituted with hydroxy, methoxy, methylthio or benzyloxy, lower cycloalkyl, (lower cycloalkyl)methyl, benzyl, 4-imidazolylmethyl, 2-thienylmethyl, 2-thiazolylmethyl, (4-hydroxyphenyl)methyl, [4-(lower alkoxy)phenyl]methyl, —CH(OH)$C_6H_5$, —($CH_2$)$_4$—$NH_2$, or —($CH_2$)$_n$C(O)O$R^{10}$ or —($CH_2$)$_n$-C(O)N$R^{11}R^{12}$ wherein n is the integer one, two or three, $R^{10}$ is hydrogen, a straight or branched chain alkyl containing one to ten carbon atoms, or phenyl(lower)alkyl and $R^{11}$ and $R^{12}$ each independently is hydrogen, lower alkyl, phenyl(lower)alkyl, or $R^{11}$ and $R^{12}$ together with the nitrogen to which they are joined form a pyrrolidino, piperidino, morpholino, piperazino or 4-(lower alkyl)piperazino;

Y is a derived amino acid radical of the formula —NH—CH($R^{13}$)—W— wherein $R^{13}$ is lower alkyl, (lower cycloalkyl)methyl, —$CH_2CH_2SCH_3$, benzyl or benzyl substituted on the aromatic portion thereof with hydroxy or lower alkoxy, and W is —CH(OH)$CH_2$C(O)— or —$CH_2$NHCH($R^{14}$)C(O)— wherein $R^{14}$ has the same meaning as defined for $R^{13}$; and $R^3$ is absent or is —N($R^{15}$)CH($R^{16}$)C(O)— wherein $R^{15}$ is hydrogen or lower alkyl and $R^{16}$ has the same meaning as defined herein for $R^9$; and $R^4$ is [—N$R^{17}$CH($R^{18}$)C(O)]$_p$—Z wherein $R^{17}$ is hydrogen or lower alkyl, $R^{18}$ has the same meaning as defined herein for $R^9$, p is the integer zero or one, and Z is hydrogen, lower alkoxy, benzyloxy or —N$R^{19}R^{20}$ wherein $R^{19}$ and $R^{20}$ each independently is hydrogen, lower alkyl or phenyl(lower)alkyl, or $R^{19}$ and $R^{20}$ together with the nitrogen atom to which they are joined form a pyrrolidino, piperidino, morpholino, piperazino or 4-(lower alkyl)piperazino; or $R^4$ is —N$R^{17}$C$R^{18}$($R^{21}$)$CH_2$OH wherein $R^{17}$ and $R^{18}$ are as defined herein and $R^{21}$ is hydrogen, lower alkyl or lower alkyl monosubstituted with hydroxy; or a therapeutically acceptable salt thereof.

A preferred group of the peptides of this invention for inhibiting HIV protease is represented by formula 1 wherein $R^1$ is the radical of formula 2 wherein $R^5$ hydrogen, lower alkyl, or $R^7$OC(O)— or $R^7$C(O)— wherein $R^7$ is lower alkyl, $R^6$ is hydrogen, lower alkyl or benzyl, L is hydrogen or one or two halo substituents as defined herein; $R^2$ is —N($R^8$)CH($R^9$)CO— wherein $R^8$ is hydrogen or methyl and $R^9$ is lower alkyl, lower cycloalkyl, cyclopropylmethyl, cyclohexylmethyl, —$CH_2CH_2COOH$, —$CH_2CH_2CONH_2$, —$CH_2CONH_2$ or benzyl; Y is —NHCH($R^{13}$)—W— wherein $R^{13}$ is lower alkyl, (lower cycloalkyl)methyl, —$CH_2CH_2$—$SCH_3$, benzyl or (4-methoxyphenyl)methyl and W is —CH(OH)—$CH_2$C(O)— or —$CH_2$NHCH($R^{14}$)C(O)— wherein $R^{14}$ is lower alkyl or (lower cycloalkyl)methyl; $R^3$ is —N($R^{15}$)CH($R^{16}$)C(O)— wherein $R^{15}$ is hydrogen or methyl and $R^{16}$ is hydrogen, lower alkyl, cyclopropylmethyl, cyclohexylmethyl, benzyl, —CH(OH)—$CH_3$ or —($CH_2$)$_n$C(O)O$R^{10}$ or —($CH_2$)$_n$-C(O)N$R^{11}R^{12}$ wherein n is the integer one, two or three, $R^{10}$ is hydrogen or a straight or branched chain alkyl containing one to ten carbon atoms, and $R^{11}$ and $R^{12}$ each independently is hydrogen, methyl or ethyl; and $R^4$ either is —N($R^{17}$)CH($R^{18}$)C(O)—Z wherein $R^{17}$ is hydrogen or methyl and $R^{18}$ is lower alkyl, lower alkyl monosubstituted with a hydroxy or a benzyloxy, cyclopropylmethyl, cyclohexylmethyl, —CH(OH)$C_6H_5$ or benzyl, and Z is hydroxy or N$R^{19}R^{20}$ wherein $R^{19}$ and $R^{20}$ each independently is hydrogen, methyl, ethyl or 2-methylbutyl, or $R^{19}$ and $R^{20}$ together with the nitrogen atom to which they are attached form a pyrrolidino or piperidino; or $R^4$ is —N$R^{17}$C$R^{18}$($R^{21}$)$CH_2$OH wherein $R^{17}$ and $R^{18}$ are as defined in the last instance and $R^{21}$ is hydrogen, lower alkyl or lower alkyl substituted with a hydroxy; or a therapeutically acceptable salt thereof.

Using the conventional three letter system for designating amino acid residues (see the second paragraph of the Details of the Invention, below), a more preferred group of the peptides is represented by formula 1 wherein $R^1$ is the radical of formula 2 wherein $R^5$ is hydrogen or tertiary-butyloxycarbonyl, $R^6$ is hydrogen, methyl, ethyl or benzyl, and L is hydrogen or one or two halo substituents at position 3 or positions 3 and 5, respectively, of the aromatic ring; $R^2$ is Val, Ala, Leu, Ile, Gly, Tbg, Cpa, Cha, Glu, Gln, Asn or Phe; Y is —NHCH($R^{13}$)—W— wherein $R^{13}$ is 1-methylethyl, Glu, Gln, 2-methylpropyl, cyclohexylmethyl, —$CH_2CH_2SCH_3$, benzyl or (4-methoxyphenyl)methyl, and W is —CH(OH)$CH_2$C(O)— or —$CH_2$NHCH($R^{14}$)-C(O)— wherein $R^{14}$ is 2-methylpropyl or cyclohexylmethyl; $R^3$ is absent or is Leu, Nle, Ile, Val, Ala, Gly, Cha, Phe, Thr, Glu, Gln, Asp or Asn; $R^4$ is Leu-$NH_2$, Leu-OH, Ile-$NH_2$, Ile-OH, Val-$NH_2$, Val-OH, Ala-$NH_2$, Ala-OH, Thr(OBzl)-$NH_2$, Cpa-$NH_2$, Cpa-OH, Cha-$NH_2$, Cha-OH, Phe-$NH_2$, Phe-NH[$CH_2$CH($CH_3$)$C_2H_5$], Phe-N($C_2H_5$)$_2$ or Phe-OH, or $R^4$ is —NHC$R^{18}$($R^{21}$)$CH_2$OH wherein $R^{18}$ is lower alkyl, —$CH_2$OH, —CH(OH)$CH_3$, —$CH_2CH_2$OH or —CH(OH)—$C_6H_5$ and $R^{21}$ is hydrogen, methyl or —$CH_2$OH; or a therapeutically acceptable salt thereof.

A most preferred group for inhibiting HIV protease is represented by compounds of formula 1 in which $R^1$ is the radical of formula 2 wherein $R^5$ is hydrogen or tertiary-butyloxycarbonyl, $R^6$ is hydrogen or benzyl and L is hydrogen or one or two halo substituents at position 3 or positions 3 and 5, respectively, of the aromatic ring; $R^2$ and Y are as defined in the last instance; $R^3$ is Leu, Nle, Ile, Val, Ala, Cha, Glu or Gln; and $R^4$ either is Ile-$NH_2$, Ala-$NH_2$, Thr(OBzl)-$NH_2$, Cha-$NH_2$ or Phe-$NH_2$, or is —NHC$R^{13}$($R^{21}$)$CH_2$OH wherein $R^{13}$ is 1-methylethyl, 1-methylpropyl, 2-methylpropyl, —$CH_2$OH or —CH(OH)$C_6H_5$ and $R^{21}$ is hydrogen or methyl; or a therapeutically acceptable salt thereof.

Included within the scope of this invention is a pharmaceutical composition for treating HIV infections in a human, comprising a compound of formula 1, or a therapeutically acceptable salt thereof, and a pharmaceutically acceptable carrier.

The scope of the invention includes as well a method for treating HIV infections in a human comprising administering thereto an effective amount of the compound of formula 1, or a therapeutically acceptable salt thereof.

Also included within the scope is a method for protecting human cells against HIV pathogenesis comprising treating said cells with an anti-HIV effective amount of a compound of formula 1, or a therapeutically acceptable salt thereof.

Furthermore, the scope of the invention includes pharmaceutical formulations and a method of treatment for renin-associated hypertension or a method of treating congestive heart failure in a mammal wherein the active agent is a peptide of formula 1. The method comprises administering to the mammal a renin-lowering effective amount of the peptide of formula 1 or a therapeutically acceptable salt thereof.

Processes for preparing the compounds of formula 1 are described hereinafter.

DETAILS OF THE INVENTION

GENERAL

The term "residue" with reference to an amino acid means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commission of Biochemical Nomenclature, see European Journal of Biochemistry, 138, 9 (1984). For instance, Val, Glu, Gln, Ala, Ile, Asp, Phe, Leu, Asn and Gly represent the residues of L-valine, L-glutamic acid, L-glutamine, L-alanine, L-isoleucine, L-aspartic acid, L-phenylalanine, L-leucine, L-asparagine and glycine, respectively. The symbols "Cpa" and "Cha" represent the residues of 2(S)-amino-3-cyclopropylpropionic acid (L-cyclopropylalanine) and 2(S)-amino-3-cyclohexylpropionic acid (L-cyclohexylalanine), respectively. The symbols "Nle" and "Tbg" represent the residues of 2(S)-aminohexanoic acid (L-norleucine) and 2(S)-amino-3,3-dimethylbutyric acid, respectively.

The term "lower alkyl" as used herein, either alone or in combination with a radical, means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl and 1,1-dimethylethyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The symbol "Boc" represents 1,1-dimethylethoxycarbonyl, known commonly as tertiary-butyloxycarbonyl. The symbol "$C_6H_5$" represents a phenyl radical.

The term "halo" as used herein means a halo radical selected from bromo, chloro, fluoro or iodo.

With reference to Y of general formula 1, the radical "—NHCH($R^{13}$)—W—" wherein $R^{13}$ is as defined hereinabove and W is —CH(OH)CH$_2$CO— represents the radical derived from the δ-amino acid known as statine (i.e. 4(S)-amino-3(S)-hydroxy-6-methylheptanoic acid) and its close analogs. The radical is derived by eliminating the hydroxyl of the carboxy group and one hydrogen of the amino group of the corresponding δ-amino acid. Each such radical has two chiral centers and thus can exist in various optically active or optically inactive forms. All forms are included for the peptides of formula 1 and for the appropriate intermediates therefore, the 4(S)-amino-3(S)-hydroxy enantiomers being preferred. The requisite 4-amino-3-hydroxy pentanoic acids for preparing the synthon to incorporate the radical into the peptide of formula 1 can be prepared by methods described by D. H. Rich and E. T. O. Sun, J. Med. Chem., 23, 27 (1980), and references therein.

The term "Sta" represents the radical —NHCH(2-methylpropyl)CH(OH)CH$_2$C(O)—, derived from statine. The term "ACHPA" represents the radical —NHCH(cyclohexylmethyl)CH(OH)CH$_2$C(O)—, derived from 4-amino-5-cyclohexyl-3-hydroxy-pentanoic acid, and the term "AHPPA" represents the radical —NHCH(benzyl)CH(OH)CH$_2$C(O)—, derived from 4-amino-3-hydroxy-5-phenylpentanoic acid. The 4(S)-amino-3(S)-hydroxy enantiomers of these last three embodiments are preferred. Unless designated otherwise by an antecedent such as (3R, 4R), the terms Sta, ACHPA and AHPPA represent their respective 4(S)-amino-3(S)-hydroxy enantiomers.

The asymmetric carbon atoms of the $R^1$, $R^2$, $R^3$ and $R^4$ units of the peptides of formula 1 have an S configuration, except those residing in the side chain of the amino acid or derived amino acid residues which may also have the R configuration.

The term "amino" as used herein means an amino radical of formula —NH$_2$. The term "lower alkylamino" as used herein means alkylamino radicals containing one to six carbon atoms and includes methylamino, ethylamino, propylamino, 1-methylethylamino and 2-methylbutylamino. The term "di(lower alkyl)amino" means an amino radical having two lower alkyl substituents each of which contains one to six carbon atoms and includes dimethylamino, diethylamino, ethylmethylamino and the like.

Additional abbreviations or symbols used hereafter for derived amino acid residues include Boc-Tyr(O-AcOH) for the $R^1$ radical N-Boc-O$^4$-(carboxymethyl)-L-tyrosyl and Boc-Tyr(O-AcOBz) for the $R^1$ radical N-Boc-O$^4$-(benzyloxycarbonylmethyl)tyrosyl. Also note that when Y is the radical —NHCH—($R^{13}$)—W— wherein $R^{13}$ is as defined hereinabove and W is —CH$_2$NHCH($R^{14}$)CO— wherein $R^{14}$ is as defined hereinabove, the radical is equivalent to two adjoining, corresponding amino acid residues wherein the amide bond joining the two residues is reduced. According to convention, the latter radical can be expressed symbolically as two amino acid residues (in the three letter system) with the symbol "ψ[CH$_2$NH]" inserted between the designation of the two adjoining amino acid residues. Accordingly, for example, the peptide of formula 1 wherein $R^1$ is N—Boc—O$^4$-(carboxymethyl)-L-tyrosyl, $R^2$ is Ala, Y is —NHCH(benzyl)CH$_2$NHCH(2-methylpropyl) with two (S)-asymmetric centers, $R^3$ is Ala, $R^4$ is Phe-NH$_2$ is designated as Boc-Tyr(O-AcOH)Ala-Pheψ[CH$_2$NH]Leu-Ala-Phe-NH$_2$.

The term "coupling agent" as used herein means an agent capable of effecting the dehydrative coupling of an amino acid or peptide free carboxy group with a free amino group of another amino acid or peptide to form an amide bond between the reactants. The agents promote or facilitate the dehydrative coupling by activating the carboxy group. Descriptions of such coupling agents and activated groups are included in general textbooks of peptide chemistry; for instance, E. Schroder and K. L. Lubke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are thionyl chloride, diphenylphosphoryl azide, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(-dimethylamino)phosphonium hexafluorophosphate, described by B. Castro et al., Tetrahedron Letters. 1219 (1975), see also D. Hudson, J. Org. Chem., 53, 617 (1988), either by itself or in the presence of 1-hydroxybenzotriazole.

The term "pharmaceutically acceptable carrier" as used herein means a non-toxic, generally inert vehicle for the active ingredient, which does not adversely affect the ingredient.

The term "effective amount" as used herein means a pre-determined amount of the peptide of this invention sufficient to be effective against HIV in vivo or renin-associated hypertension.

PROCESS

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schroder and K. Lubke, cited above, in the textbook series, "The Peptides: Analysis, Synthesis, Biology", E. Gross et al., Eds., Academic Press, New York, N.Y., 1979-1987, Volumes 1 to 8, and by J. M. Stewart and J. D. Young in "Solid Phase Peptide Synthesis", 2nd ed., Pierce Chem. Co., Rockford, IL, USA, 1984.

A common feature of the aforementioned processes for the peptides is the protection of the labile side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

Another feature of the preparation of the peptides of formula 1 is the incorporation into the peptide of the unit Y. As noted previously the unit Y can be either of two subunits, i.e. $-NHCH(R^{13})CH(OH)CH_2C(O)-$ wherein $R^{13}$ is as defined herein or $-NHCH(R^{13})CH_2NHCH(R^{14})C(O)-$ wherein $R^{13}$ and $R^{14}$ are as defined herein. The first-mentioned subunit can readily be incorporated into the peptide by coupling the N-protected derivative of the corresponding 4-amino-3-hydroxypentanoic acid (of formula $NH_2-CH(R^{13})CH(OH)CH_2C(O)OH$), noted above, at the appropriate point during the preparation of the peptide by the classical methods of coupling of amino acid residues or fragments. The second-mentioned subunit, $-NHCH(R^{13})CH_2NH-CH(R^{14})C(O)-$ can be incorporated by forming the linear peptidyl framework of the peptide of formula 1, or a fragment thereof, by a reductive alkylation between two sub-fragments, each sub-fragment containing a precursor portion of the Y unit and at least one of the sub-fragments containing one or more of the amino acid units, whereby the $CH_2NH$ bond of the Y unit is formed; for example, the reductive N-alkylation of the dipeptide of formula $NH_2CH(R^{14})C(O)-R^3-R^4$ with $Boc-NHCH(R^{13})-CHO$ in the presence of sodium cyanoborohydride to give the fragment $Boc-NHCH(R^{13})CH_2NHCH(R^{14})C(O)-R^3-R^4$.

With reference to the process products, the peptides of formula 1 can be prepared by:

(i) coupling the derived amino acid of formula 2a

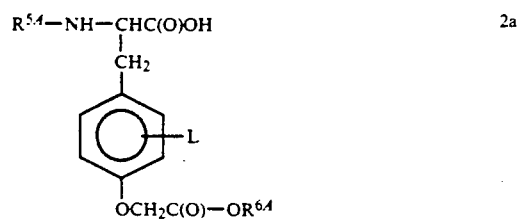

wherein $R^{5A}$ is lower alkyl or $R^7OC(O)-$ or $R^7C(O)-$ wherein $R^7$ is as defined hereinabove, $R^{6A}$ is lower alkyl, lower cycloalkyl, (lower cycloalkyl)methyl, phenyl, phenyl monosubstituted with lower alkyl, lower alkoxy or halo, benzyl or benzyl monosubstituted with lower alkyl, lower alkoxy or halo, and L is as defined herein; with a fragment of formula $H-R^{2A}-Y-R^{3A}-R^{4A}$ wherein $R^{2A}$, $R^{3A}$ and $R^{4A}$ have the same meaning as defined herein for $R^2$, $R^3$ and $R^4$ respectively, except that side chain amino and carboxy groups, and a C-terminal carboxy group, if present, are replaced with corresponding protected groups and Y is as defined herein; followed, if required, by amino deprotection and/or carboxy deprotection, to give the corresponding peptide of formula 1. Note that benzyl or substituted benzyl of $R^{6A}$ can serve a dual role, i.e. serve as the progenitor for the corresponding radical in the ultimate product of the synthesis or serve as a carboxy protecting group. When required, such carboxy protecting groups can be selectively removed by known methods (e.g. hydrogenation) in the presence of other carboxy protecting groups (e.g. classical acid sensitive protecting groups) in the pentultimate or next to the pentultimate intermediate of the process. Also note that the radicals $R^7OC(O)-$ and $R^7C(O)-$ can serve a dual role as a progenitor for the corresponding radical in the final product or serve as an amino protecting group.

Alternatively, the peptides of formula 1 in which $R^1$ is the derived amino acid radical of formula 2 in which $R^5$, $R^6$ and L are as defined herein, and $R^2$, Y, $R^3$ and $R^4$ are as defined herein can be prepared by subjecting the intermediate of formula 3

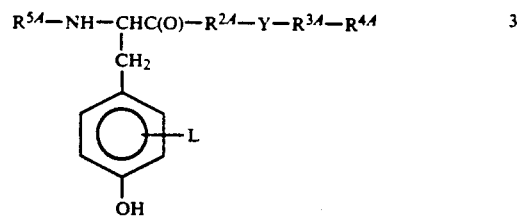

wherein $R^{5A}$, L, $R^{2A}$, Y, $R^{3A}$ and $R^{4A}$ are as defined hereinabove, to O-alkylation with an alkylating agent of formula $XCH_2C-(O)OR^{6A}$ wherein X is bromo, chloro or iodo and $R^{6A}$ is as defined hereinabove, in the presence of a suitable strong base; followed, if required, by deprotection to obtain the desired corresponding peptide of formula 1.

The intermediate of formula 3 can be prepared by conventional methods; for example, see D. F. Veber et al., European patent application, 77,028, published Apr. 20, 1983. Suitable strong bases for the above-noted alkylation include alkali metal carbonates, preferably potassium carbonate; alkali metal hydroxides, preferably sodium hydroxide or potassium hydroxide; or alkali metal hydrides, preferably sodium hydride.

The peptide of formula 1 of this invention can be obtained in the form of a therapeutically acceptable salt.

In the instance where a particular peptide has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts are those with the sodium, potassium or calcium cations, or with strong organic bases, for example, triethylamine or N-methylmorpholine.

In general, the therapeutically acceptable salts of the peptides of formula 1 are biologically fully equivalent to the peptides themselves.

BIOLOGICAL ASPECTS

The HIV protease inhibiting properties and the cell protective effect against HIV pathogenesis of the peptides of formula 1, or a therapeutically acceptable salt thereof, can be demonstrated by biochemical, microbiological and biological procedures.

A particular useful procedure for demonstrating the HIV protease inhibiting properties of the peptides of formula 1 or their therapeutically acceptable salts is the "Recombinant HIV Protease HLPC Assay". The procedure is based on the capacity of the test compound to inhibit enzymatic cleavage by HIV protease of a decapeptide (the substrate) having an amino acid sequence which includes a known HIV protease cleavage site of the HIV polyprotein; see H. G. Krausslich et al., Proc. Natl. Acad. Sci. USA, 86, 807 (1989). Details of this assay together with the results obtained for exemplified peptides of formula 1 are described in the examples hereinafter.

The cell protective effect of the peptides or their therapeutically acceptable salts can be demonstrated by microbiological procedures for evaluating the effect of test compounds in inhibiting the cytopathogenicity of HIV in human T4 cell lines; for example, see M. Baba et al., Biochem, Biophys. Res. Comm., 142, 128 (1987).

When a peptide of this invention, or a therapeutically acceptable salt thereof, is used to combat HIV infections in a human, the peptide can be administered orally, topically or parenterally, in a vehicle comprising one or more pharmaceutically acceptable carriers, the proportion of which is determined by the solubility and chemical nature of the peptide, chosen route of administration and standard biological practice. For oral administration, the peptide or a therapeutically acceptable salt thereof can be formulated in unit dosage forms such as capsules or tablets each containing a predetermined amount of the active ingredient, ranging from about 25 to 500 mg, in a pharmaceutically acceptable carrier. For topical administration, the peptide can be formulated in a pharmaceutically acceptable vehicle containing 0.1 to 10 percent, preferably 0.5 to 5 percent, of the active agent. Such formulations can be in the form of a cream, lotion, sublingual tablet, or preferably a transdermal patch or buccal patch.

For parenteral administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g. in "Remington's Pharmaceutical Sciences", 16th ed, Mack Publishing Company, Easton, Penn., 1980.

The dosage of the peptide will vary with the form of administration and the particular active agent chosen. Furthermore, it will vary with the particular host under treatment. Generally, treatment is initiated with small dosages substantially less than the optimum dose of the peptide. Thereafter, the dosage is increased by small increments until the optimum effect under the circumstances is reached. In general, the peptide is most desirably administered at a concentration level that will generally afford antivirally effective results without causing any harmful or deleterious side effects.

For oral adminstration, the peptide or a therapeutically acceptable salt is administered in the range of 1.0 to 75 mg per kilogram of body weight per day, with a preferred range of 2.5 to 20 mg per kilogram.

With reference to systemic adminstration, the peptide of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, zidovudine, dideoxycytidine, phosphonoformate, ribavarin, antiviral interferons (e.g. α-interferon or interleukin-2) or aerosol pentamidine.

The peptides of formula 1 also possess the ability to inhibit renin activity. The renin inhibiting activity of the compounds can be demonstrated in standard pharmacological tests such as those described by M. G. Bock et al., J. Med. Chem., 31, 1918 (1988). As such the peptides are indicated for the diagnosis, prophylaxis and treatment of renin-associated hypertension and for the treatment of congestive heart failure in mammals including humans. For the latter purposes or indication, the peptides can be formulated and administered in the same manner as described above, but usually at higher dosages which can be determined conventionally by using well known pharmacological protocols.

A preferred group of the peptides for inhibiting renin is represented by formula 1 wherein $R^1$ is the radical of formula 2 wherein $R^5$ is $R^7OC(O)$— wherein $R^7$ is lower alkyl, $R^6$ is hydrogen or benzyl and L is hydrogen; $R^2$ is —$N(R^8)CH(R^9)CO$— wherein $R^8$ is hydrogen and $R^9$ is lower alkyl, lower alkyl monosubstituted with hydroxy, benzyl, 4-imidazolymethyl, 2-thienylmethyl or 2-thiazolymethyl, Y is Sta, ACHPA or AHPPA, $R^3$ is absent or is —$N(R^{15})CH(R^{16})CO$— wherein $R^{15}$ is hydrogen and $R^{16}$ is lower alkyl, and $R^4$ is either —$NR^{17}CH(R^{18})$—$C(O)$—$Z$ wherein $R^{17}$ is hydrogen, $R^{18}$ is lower alkyl, lower alkyl monosubstituted with hydroxy or benzyloxy, —$CH(OH)C_6H_5$ or benzyl, and Z is hydrogen or amino, or $R^4$ is —$NR^{17}CR^{18}(R^{21})$—$CH_2OH$ wherein $R^{17}$ is hydrogen, $R^{18}$ is lower alkyl, lower alkyl monosubstituted with a hydroxy, —$CH(OH)C_6H_5$ or benzyl and $R^{21}$ is hydrogen or lower alkyl, or a therapeutically acceptable salt thereof.

A more preferred group of peptides for inhibiting renin is represented by formula 1 wherein $R^1$ is the radical of formula 2 wherein $R^5$ is tertiary-butyloxycarbonyl, $R^6$ is hydrogen, methyl or benzyl and L is hydrogen, $R^2$ is Val, Ala or Phe, Y is as defined in the last instance, $R^3$ is absent or Ala, Ile or Leu, and $R^4$ is Ala-$NH_2$, Phe-$NH_2$ or —$NHCR^{18}(R^{21})CH_2OH$ wherein $R^{18}$ is —$CH_2OH$, —$CH(OH)CH_3$ or —$CH(OH)C_6H_5$ and $R^{21}$ is hydrogen or methyl, or a therapeutically acceptable salt thereof.

The following examples illustrate further this invention. Solution percentages or ratios express volume to volume relationship, unless stated otherwise. Abbreviations used in the examples include Boc: t-butyloxycarbonyl; BOP: (benzotriazol1-yloxy)tris(dimethylamino)-phosphonium hexafluorophosphate; Bzl: benzyl; DMF: dimethyl formamide; $Et_2O$: diethyl ether; Fm: 9-fluorenylmethyl; HPLC: high performance liquid chromatography; MeOH: methanol; TFA: trifluoroacetic acid; THF: tetrahydrofuran.

EXAMPLE 1

Preparation of
N-[N-[N-[N-Boc-$O^4$-(Benzyloxycarbonylmethyl)-L-tyrosyl]-L-valyl]-4(S)-amino-3(S)-hydroxy-5-cyclohexylpentanoyl]-L-leucyl]-L-phenylalaninamide (Boc-Tyr(OAcOBzl)-Val-ACHPA-Leu-Phe-$NH_2$.

a) Boc-Phe-$NH_2$: Isobutyl chloroformate (2.86 mL, 22 mmol) was added dropwise at 0° C. to a stirred solution of N-methylmorpholine (2.42 mL, 22 mmol) and Boc-Phe-OH (5.31 g, 20 mmol) in dry THF. The resulting solution was stirred for an additional 30 min at 0° C. Thereafter, a 28% aqueous solution of ammonia (5 mL) was added dropwise over 5 min. The solvent was evaporated and the residue was dissolved in ethyl acetate. The solution was washed successively with a 5% aqueous solution of citric acid (three times), saturated aqueous $NaHCO_3$ (three times) and saturated aqueous NaCl. The organic solution was dried over $Na_2SO_4$ and evaporated to afford Boc-Phe-$NH_2$ (5.0 g, 94%) as a white solid.

b) Boc-Leu-Phe-$NH_2$: A solution of Boc-Phe-$NH_2$ (6.46 g, 24.4 mmol) in 6N HCl/dioxane (84 mL) was stirred at room temperature (20°–22° C.) under a nitrogen atmosphere for 30 min. The solvent was evaporated and the residue was dried under high vacuum. The solid residue was suspended in dry $CH_3CN$ (300 mL) and the resulting mixture was cooled to 0°–5° C. and stirred under a nitrogen atmosphere. Dry $Et_3N$ (3.7 mL, 26 mmol) was added, followed by Boc-Leu-OH(monohydrate) (5.4 g, 22 mmol), BOP (10.69 g, 24.2 mmol) and more $Et_3N$ (7.4 mL, 53 mmol). After 1.5 h, more BOP (4.28 g, 9.7 mmol) and $Et_3N$ (1.48 mL, 10.6 mmol) were added. The reaction was stirred for an additional 15 min, then the $CH_3CN$ was evaporated under reduced pressure and the residue was partitioned between a saturated aqueous solution of NaCl (200 mL) and ethyl acetate (3 times 200 mL). The combined organic solutions were washed successively with 100 mL each of a 10% aqueous solution of citric acid, water, a 5% aqueous solution of $NaHCO_3$ (three times) and water. The organic solution was dried over $MgSO_4$ and concentrated under reduced pressure. Chromatography of the residue over silica gel (eluent=ethyl acetate) gave a white gum which was triturated with $Et_2O$/hexane. The resulting solid was collected to afford Boc-Leu-Phe-$NH_2$ (7.7 g, 93%) as a white solid. Mass spectrum: 378 (M+H)$^+$. Amino acid analysis: Leu, 100; Phe, 1.00.

c) Boc-ACHPA-Leu-Phe-$NH_2$: A solution of Boc-Leu-Phe-$NH_2$ (100 mg, 0.26 mmol) in 6N HCl/dioxane (1 mL) was stirred at room temperature under a nitrogen atmosphere for 15 min. The solvent was evaporated and the residue was dried under high vacuum for 1 h. The solid was suspended in dry $CH_3CN$ (2 mL) and stirred under a nitrogen atmosphere. The solution was adjusted to pH 8 (wet pH paper) by the addition of N-methylmorpholine, then Boc-ACHPA-OH (83 mg, 0.26 mmol) was added. The solution was stirred at room temperature for 1 h (during which time pH 8 was maintained by the occasional addition of N-methylmorpholine). The mixture was poured into a saturated aqueous solution of NaCl. The aqueous solution was extracted twice with ethyl acetate. The combined organic extracts were washed successively with ice-cold 0.5N aqueous HCl, 10% aqueous $Na_2CO_3$ (twice) and saturated aqueous NaCl (three times). The organic solution was dried over $Na_2SO_4$ and the solvent was evaporated. Chromatography of the residue over silica gel, eluting with 5% methanol in chloroform, afforded Boc-ACHPA-Leu-Phe-$NH_2$ (138 mg, 92%) as a white solid.

d) Boc-Val-ACHPA-Leu-Phe-$NH_2$: A solution of Boc-ACHPA-Leu-Phe-$NH_2$ (72 mg, 0.125 mmol) in 6 NHCl/dioxane (1 mL) was stirred at room temperature under a nitrogen atmosphere for 15 min. The solvent was evaporated and the residue was dried under high vacuum for 1 h. The solid was suspended in dry $CH_3CN$ (2 mL) and stirred under a nitrogen atmosphere. The solution was adjusted to pH 8 (wet pH paper) by the addition of N-methylmorpholine, then Boc-Val-OH (27 mg, 0.13 mmol) was added, the pH was again adjusted to pH 8 (as before) and BOP (55 mg, 0.13 mmol) was added. The solution was stirred at room temperature for 1 h (during which time pH 8 was maintained by the occasional addition of N-methylmorpholine). The mixture was poured into a saturated aqueous solution of NaCl. The aqueous solution was extracted twice with ethyl acetate. The combined organic extracts were washed successively with ice-cold 0.5N aqueous HCl, 10% aqueous $Na_2CO_3$ (twice) and saturated aqueous NaCl (three times). The organic solution was dried over $Na_2SO_4$ and the solvent was evaporated. Chromatography of the residue over silica gel, eluting with 5% methanol in chloroform, afforded Boc-Val-ACHPA-Leu-Phe-$NH_2$ (71 mg, 84%) as a white solid.

e) Boc-Tyr-Val-ACHPA-Leu-Phe-NH$_2$: A solution of Boc-Val-ACHPA-Leu-Phe-NH$_2$ (175 mg, 0.26 mmol) in 6N HCl/dioxane (1 mL) was stirred at room temperature under a nitrogen atmosphere for 15 min. The solvent was evaporated and the solid residue was dried under high vacuum for 1 h. The solid was suspended in dry CH$_3$CN (3 mL). The mixture was stirred under a nitrogen atmosphere. The solution was adjusted to pH 8 (wet pH paper) by the addition of N-methylmorpholine, then Boc-Tyr-OH (73 mg, 0.26 mmol) was added, the pH was again adjusted to pH 8 (as before) and BOP (115 mg, 0.26 mmol) was added. The solution was stirred at room temperature for 90 min (during which time pH 8 was maintained by the occasional addition of N-methylmorpholine). The mixture, which became a gel, was mixed with ethyl acetate. The mixture was sonicated to give a homogenous suspension. The solid in the suspension was collected on a filter, washed with ethyl acetate and dissolved in 10% methanol in chloroform. The solution was filtered through silica gel to afford Boc-Tyr-Val-ACHPA-Leu-Phe-NH$_2$ (144 mg, 66%) as a white solid upon evaporation of the eluent. Mass spectrum: 837 (M+H)$^+$.

The latter compound (130 mg, 0.155 mmol) was mixed with K$_2$CO$_3$ (86 mg, 0.62 mmol) in DMF (1 mL). Benzyl bromoacetate (37 μL, 0.230 mmol) was added to the stirred mixture. The resulting mixture was stirred at room temperature under an atmosphere of nitrogen for 14 h. The mixture was poured into water (50 mL) and the resulting suspension stirred vigorously for 5 min. The precipitated solid was collected on a filter and washed successively with portions of ethyl acetate and Et$_2$O. The solid was redissolved in DMSO and precipited by the addition of water. The solid was collected by filtration and dried under high vacuum to afford the title compound (110 mg, 72%) as a white solid. Mass spectrum: 985 (M+H)$^+$. Amino acid analysis: Leu, 1.03; Phe, 0.94; Val, 1.03; ACHPA, 0.96; Tyr(O-AcOH), 0.79.

EXAMPLE 2

H-Tyr(O-AcOBzl)-Val-ACHPA-Leu-Phe-NH$_2$.HCl

A solution of Boc-Tyr(O-AcOBzl)-Val-ACHPA-Leu-Phe-NH$_2$ (20 mg, 0.020 mmol) in 6N HCl/dioxane (1.5 mL) was stirred at room temperature under a nitrogen atmosphere for 20 min. The solvent was evaporated and the residue was dried under oil pump vacuum for 1 h. The solid was triturated with Et$_2$O and the resulting suspension was filtered. The precipitate was collected and dried under high vacuum for 17 h at room temperature to afford the title compound (12 mg, 65%) as a white solid. Mass spectrum: 886 (M-Cl)$^+$. Amino acid analysis: Leu, 1.03; Phe, 0.93; Val, 1.04; ACHPA, 0.91; Tyr(OAcOH), 0.80.

EXAMPLE 3

Boc-Tyr(O-AcOH)-Val-ACHPA-Leu-Phe-NH$_2$

MeOH (16 mL) was added to a solution of Boc-Tyr(O-AcOBzl)-Val-ACHPA-Leu-Phe-NH$_2$ (74 mg, 0.075 mmol) in DMF (4 mL). Under an atmosphere of argon, 10% palladium on carbon (7.4 mg) was added. The mixture was shaken on a Parr apparatus under an atmosphere of H$_2$ (at 45 psi) for 2 h. The mixture was filtered through a 45 μm membrane and the filtrate was evaporated. The residue was dried under high vacuum to afford the title compound (47 mg, 70%). Mass spectrum: 917 (M+Na)$^+$. Amino acid analysis: Val, 0.95; Leu, 1.02; Phe, 1.02; Tyr(O-AcOH), present.

EXAMPLE 4

H-Tyr(O-AcOH)-Val-ACHPA-Leu-Phe-NH$_2$.HCl

A solution of Boc-Tyr(O-AcOH)-Val-ACHPA-Leu-Phe-NH$_2$ (25 mg, 0.028 mmol) in 6N HCl/dioxane (1.5 mL) was stirred at room temperature under a nitrogen atmosphere for 20 min. The solvent was evaporated and the residue was dried under reduced pressure for 1 h. The solid was triturated with Et$_2$O and the resulting suspension was filtered. The collected precipitate was dried under reduced pressure to afford the title compound (20 mg, 86%). Mass spectrum: 795 (M-Cl)$^+$. Amino acid analysis: Val, 0.94; Leu, 1.02; Phe, 1.04; Tyr(O-AcOH), present.

EXAMPLE 5

Boc-Tyr(O-AcOH)-Phe-ACHPA-Leu-Phe-NH$_2$

The title compound was prepared by the procedures described in examples 1 to 3 but substituting Boc-Phe-OH for Boc-Val-OH. Mass spectrum: 943 (M+H)$^+$. Amino acid analysis: Leu, 0.99; Phe, 2.01; ACHPA, 0.86; Tyr(O-AcOH), 0.86.

Other examples of peptides of formula 1 include:

H—Tyr—(O—AcOBzl)—Val—Sta—Asp—Leu—N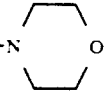O

H-Tyr-(O-AcOBzl)-Ala-ACHPA-Leu-Phe-NHC(CH$_2$OH)$_2$CH$_3$
H-Tyr-(O-AcOH)-(N-Me)Asp-ACHPA-Cha-Asn-NH$_2$
H-(3-iodo)-Tyr(O-AcOBzl)-Val-ACHPA-Leu-Phe-NH$_2$
H-(3,5-diiodo)-Tyr(O-AcOBzl)-Val-ACHPA-Leu-Phe-NH$_2$
Boc-Tyr(O-AcOEt)-Ala-AHPPA-Gln-Ile-OH
H-Tyr(O-AcOH)-Cpa-ACHPA-Tyr-NHCH$_3$
Boc-Tyr(O-AcOH)-Val-ACHPA-NHC(CH$_2$OH)$_2$CH$_3$

EXAMPLE 6

Recombinant HIV Protease HPLC Assay:

Enzyme: HIV protease was expressed in E. coli and purified to ca. 50% purity according to the procedure described by H.-G. Krausslich et al., Proc. Natl. Acad. Sci. USA, 86, 807 (1989). The enzyme was stored as 10 μL aliquots at −70° C. The aliquots were diluted to 1/10th of the original concentration with buffer prior to use (enzyme working solution).

Substrate: VSFNFPQITL-NH$_2$, MW 1164, see Krausslich et al., supra, was used as substrate. The substrate was made into 10 mM stock in DMSO and stored at −20° C. Prior to use, the stock was diluted with buffer to give a 400 μM solution substrate working solution.

Buffer: 2-(4-Morpholino)ethanesulfonic acid (50 mM), NaCl (25 mM) and EDTA (5 mM) was dissolved in distilled H$_2$O (90 mL) and the solution was adjusted to pH6 with concentrated aqueous NaOH. The latter solution was diluted to 100 mL with H$_2$O to give the buffer.

Procedure: (1) The test compound was dissolved in DMSO to give a solution having 40X the final concentration of the test compound in the assay mixture (see step 2) so that the amount of DMSO in the assay mixture was 5% (v,v) or less. (2) The assay mixture was prepared by mixing 10 μL of the substrate working solution, 0.5 μL of the solution of the test compound in DMSO from step 1, and 10 μL of the enzyme working solution. (3) The assay mixture was incubated at 37° C. for 1 h. (4) The reaction was quenched by adding 100 μL of 2% aqueous TFA. (5) The substrate and products (i.e. VSFNF and PQITL-NH$_2$) were separated by subjecting 100 μL of the quenched assay mixture to HPLC using Nucleosil® C$_{18}$ column with a 26-min linear gradient at 1 mL/min from 11% to 70% acetonitrile in H$_2$O with 0.05% aqueous TFA. Elution was monitored at 210 nm. (6) A control which was the assay mixture without the test compound, was subjected simultaneously to steps 3 to 5.

Inhibition Studies: Cleavage products and remaining parent substrate were quantified by either peak height or by integration of the appropriate HPLC peaks. Substrate conversion was calculated using the following relationship:

$$\% \text{ Conversion} = \frac{\text{Sum of peak height or peak area of products}}{\text{Sum of peak height or peak area of substrate and products}} \times 100$$

Enzyme inhibition of the test compound was calculated as follows:

$$\% \text{ Inhibition} = 100 - \frac{\% \text{ Conversion for assay mixture}}{\% \text{ Conversion of control}} \times 100$$

The concentration of the test compound which causes a 50% inhibition of the HIV-protease, i.e. the IC$_{50}$, was determined as follows:

The percent inhibition of the enzyme was determined for a minimum of three different concentrations of the test compound. Thereafter, the IC$_{50}$ was determined graphically by plotting the percent inhibition of the substrate against the concentration of the test compound.

The following table of exemplified peptides of formula 1 lists their IC$_{50}$ as determined in the recombinant HIV protease HLPC assay.

| Peptide | Example in which peptide is prepared | IC$_{50}$ (nM) |
| --- | --- | --- |
| Boc-Tyr(O—AcOBzl)-Val-ACHPA-Leu-Phe-NH$_2$ | 1 | 70 |
| H-Tyr(O—AcOBzl)-Val-ACHPA-Leu-Phe-NH$_2$.HCl | 2 | 5 |
| Boc-Tyr(O—AcOH)-Val-ACHPA-Leu-Phe-NH$_2$ | 3 | 52 |
| H-Tyr(O—AcOH)-Val-ACHPA-Leu-Phe-NH$_2$.HCl | 4 | 10 |
| Boc-Tyr(O—AcOH)-Phe-ACHPA-Leu-Phe-NH$_2$ | 5 | 1000 |

What is claimed is:

1. A peptide selected from the group consisting of:
Boc-Tyr(O-AcOBzl)-Val-ACHPA-Leu-Phe-NH$_2$
H-Tyr(O-AcOBzl)-Val-ACHPA-Leu-Phe-NH$_2$
Boc-Tyr(O-AcOH)-Val-ACHPA-Leu-Phe-NH$_2$
H-Tyr(O-AcOH)-Val-ACHPA-Leu-Phe-NH$_2$.
Boc-Tyr(O-AcOH)-Phe-ACHPA-Leu-Phe-NH$_2$ 2. A pharmaceutical composition comprising a peptide as recited in claim 1, or a therapeutically acceptable salt thereof, and a pharmaceutically acceptable carrier.

* * * * *